United States Patent [19]

Hutton

[11] Patent Number: 5,326,869
[45] Date of Patent: Jul. 5, 1994

[54] CHEMICAL PROCESS

[75] Inventor: Jonathan Hutton, Adlington, England

[73] Assignee: Imperial Chemical Industries, PLC, London, England

[21] Appl. No.: 979,096

[22] Filed: Nov. 20, 1992

[30] Foreign Application Priority Data

Nov. 25, 1991 [GB] United Kingdom ............... 9124968

[51] Int. Cl.$^5$ ........................................ C07D 487/04
[52] U.S. Cl. .................................... 544/209; 544/206
[58] Field of Search ............................ 544/209, 198

[56] References Cited

FOREIGN PATENT DOCUMENTS 459702 12/1991 European Pat. Off. .

OTHER PUBLICATIONS

Imamoto, et al., Tet. Lett., 22, 1803, 1981, "Trimethyl Polyphosphate (PPSE). A Useful Reagent For the Beckmann Rearrangement".
K. Yamamoto, et al., Chem. Lett., 1225, 1982, "Composition of Polyphosphoric Acid Trimethylsilyl Ester . . . ".
T. Imamoto, et al., Tet. Lett., 23, 1467, 1982, "The Reaction of Aryl Methyl Ketones with Aromatic Aldehydes in Trimethylsilyl Polyphosphate (PPSE) . . . ".
M. Yokoyama, et al., Synthesis, 591, 1982, "Organic Reactions Using Trimethylsilyl Polyphosphate (PPSE): A Convenient Synthesis of Nitriles from Carboxamides".
T. Inamoto, et al., Synthesis, 460, 1983, "A Convenient Method for the Preparation of Alkyl Iodides From Alcohols".
J. M. Aizpuru, et al., Bull. Soc. Chim. Fr., II–142, 1983, "Reagents and Synthetic Methods . . . ".
M. Kakimoto, et al., Chem. Lett. 821, 1984, "A Novel Direct Synthesis of Amidines from Carboxylic Acids And Amines Using Polyphosphoric Acid . . . ".
T. Imamoto, et al., J. Org. Chem., 49, 1105, 1984, "Preparation and Synthetic Use of Trimethylsilyl Polyphosphate. A New Stereoselective Aldol-Type . . . ".
M. Kakimoto, et al., Chem. Lett. 1831, 1984, "Pummerer Rearrangement Promoted by Polyphosphoric Acid Trimethylsilyl Ester (PPSE)".
Y. Okamoto, Bull. Chem. Soc., Jpn., 58, 3393, 1985, "Synthesis of Alkyl Dihydrogenphosphate by the Reaction of Alcohols and Silyl Polyphosphate".
S. Ogata, et al., Bull. Chem. Soc. Jpn., 59, 2171, 1986, "Synthesis of Amides and Amidines by Reaction of Carboxylic Acids and Amines . . . ".
M. Kakimoto et al., Synthesis, 164, 1987, "Synthesis of Dithioacetals from Carbonyl Compounds and Thiols In the Presence of Polyphosphoric Acid . . . ".
M. Kakimoto, et al., Bull. Chem. Jpn., 61, 2643, 1988, "Pinacol-Pinacolone Rearrangement Promoted by Polyphosphoric Acid Trimethylsilyl Ester (PPSE)".
E. M. Berman et al., J. Org. Chem., 54, 5642, 1989, "Trimethylsilyl Polyphosphate for Intramolecular Friedel–Crafts Cyclizations".
C. Fluozat et al., Synthesis, 64, 1990, "A New Convenient Synthesis of 2-Aryl-And 2-Heteroaryloxazolo . . . ".
Deshpande, et al., Synthesis, 863, 1974, "Synthesis of s-Triazolo . . . ".
Imai et al., Synthesis, 851, 1983, "A Convenient Synthesis of 2H-1,2,4-Benzothiadiazine . . . ".

Primary Examiner—John M. Ford
Attorney, Agent, or Firm—Cushman, Darby & Cushman

[57] ABSTRACT

A process for the preparation of a 5,7-diaryloxy-2-(2-heteroaryl)-triazolo[1,5-a][1,3,5]triazine, which comprises reacting a N-2-(4,6-diaryloxy)-[1,3,5]triazinyl-N'-(2-heteroarylcarbonyl)hydrazine with a polyphosphoric acid silyl ester. The invention also provides a multistep process for preparing certain triazolotriazines having activity asadenosine antagonists.

11 Claims, No Drawings

CHEMICAL PROCESS

The present invention relates to a process for the preparation of certain 5,7-diaryloxy-2-(2-heteroaryl)-triazolo[1,5-a][1,3,5]triazines, which are useful as intermediates in the preparation of certain pharmaceutically active compounds. The invention also relates to a process for preparing these pharmaceutically active compounds.

European patent application publication no. 459702A1, (published on Dec. 4, 1991) discloses compounds of general formula I (formula set out hereinafter, together with the other formulae referred to herein by Roman numerals) wherein:

Q is a 5-membered heteroaryl optionally bearing 1 or 2 substituents independently selected from (1-4C)alkyl and halogeno;

$R^1$ is hydrogen, (1-6C)alkyl, or (1-4C)alkanoyl;

$R^2$ is hydrogen, (3-12C)cycloalkyl, (3-6C)alkenyl, phenyl(3-6C)alkenyl, tetrafluorophenyl, pentafluorophenyl, 5- or 6-membered heteroaryl, optionally substituted (1-6C)alkyl or optionally substituted phenyl, said optionally substituted alkyl being unsubstituted or substituted by one of (3-6C)cycloalkyl, optionally substituted 5- or 6-membered heteroaryl, optionally substituted phenyl and a group of formula $R^{10}(CO)_nX_b(CO)_m$ in which $R^{10}$ is (1-6C)alkyl, (3-6C)cycloalkyl, optionally substituted phenyl or optionally substituted phenyl(1-4C)alkyl, n+m is 0 or 1, provided that when m is 0, X and Xb are separated by at least two carbon atoms, Xb is oxy, thio, sulphinyl, sulphonyl or an imino group of formula —NRb in which Rb is hydrogen, (1-6C)alkyl or together with $R^{10}$ and the adjacent nitrogen atom forms a 4 to 6-membered saturated heterocyclic ring, said optionally substituted 5- or 6-membered heteroaryl being unsubstituted or substituted by 1 or 2 of (1-4C)alkyl, (1-4C)alkoxy and halogeno, and any of said optionally substituted phenyl being unsubstituted or substituted by (1-4C)alkylenedioxy or by 1,2 or 3 of halogeno, cyano, trifluoromethyl, (1-4C)alkoxycarbonyl, hydroxy, (1-4C)alkanoyloxy, benzyloxy, halogenobenzyloxy, nitro, and (1-4C)alkyl or alkoxy optionally bearing a group of formula $R^{11}CO$ in which $R^{11}$ is (1-4C)alkoxy, (3-6C)alkylamino, (3-6C)cycloalkylamino or [N-(1-4C)alkyl][N-(1-4C)dialkylamino(-1-4C)alkyl]amino, and sulphamoyl of formula —$SO_2.NR^3R^4$ in which $R^3$ and $R^4$ are independently hydrogen or (1-4C)alkyl, or $R^3$ is hydrogen and $R^4$ is [(2-5C)alkoxycarbonyl]methyl, carbamoylmethyl or [N-(1-4C)alkylcarbamoyl]methyl; and X is oxy, thio, sulphinyl, sulphonyl or an imino group of formula —NRa— in which Ra is hydrogen (1-6C)alkyl or together with $R_2$ and the adjacent nitrogen atom forms a 4 to 6-membered saturated heterocyclic ring; and A is N;

and pharmaceutically acceptable salts thereof.

The compounds of formula I possess the property of antagonising one or more of the physiological actions of adenosine (especially those mediated by the adenosine $A_2$ receptor) and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

One group of compounds of general formula I disclosed in EP A1 459702 consists of those wherein Q is a 5-membered heteroaryl (e.g. furyl or thienyl) optionally bearing 1 or 2 substituents independently selected from (1-4C)alkyl and halogeno; X is oxy, thio or an imino group of the formula —NRa— in which Ra is hydrogen or (1-6C)alkyl; $R^1$ is hydrogen, (1-6C)alkyl or (1-4C)alkanoyl; and $R^2$ is:

(a) phenyl, pyridyl, isoxazolyl, thiadiazolyl, tetrafluorophenyl, pentafluorophenyl, or phenyl bearing 1, 2 or 3 substituents independently selected from (1-4C)alkyl, (1-4C)alkoxy, halogeno, cyano, trifluoromethyl, nitro, benzyloxy, halogenobenzyloxy, hydroxy, and a sulphamoyl group of the formula —$SO_2.NR^3R^4$ in which $R^3$ and $R^4$ are independently hydrogen or (1-4C)alkyl, or $R^3$ is hydrogen and $R^4$ is [(2-5C)alkoxycarbonyl]methyl, carbamoylmethyl or [N-1-4C)alkylcarbamoyl]methyl;

(b) (1-6C)alkyl, (3-12C)cycloalkyl, (3-6C)cycloalkyl(1-4C)alkyl, furyl, thienyl, phenyl(1-4C)alkyl, furyl(1-4C)alkyl, thienyl(1-4C)alkyl, a furyl, thienyl or phenyl moiety of which may itself optionally bear 1 or 2 substituents independently selected from (1-4C)alkyl, (1-4C)alkoxy and halogeno; or (c) a group of the formula $R^5.Xa.CH_2.CH_2$— in which $R^5$ is (1-6C)alkyl or phenyl which latter may optionally bear 1 or 2 substituents independently selected from (1-4C) alkyl, (1-4C) alkoxy and halogeno, and Xa is oxy, thio, sulphinyl, sulphonyl, imino or N-(1-6C)alkylimino, or in which the group $R^5.Xa$— is morpholino, thiomorpholino, pyrrolidino, piperidino or azetidino.

A particular value for Q when it is a 5-membered heteroaryl is, for example, furyl, thienyl, oxazolyl, thiazolyl, isoxazolyl or isothiazolyl, which heteroaryl moieties may optionally bear 1 or 2 substituents independently selected from methyl, ethyl, fluoro, chloro and bromo. An example of a particularly preferred value for Q is furyl, optionally substituted as defined above. The 2-furyl group is preferred.

A particular value for $R^1$ when it is alkyl is, for example, methyl, ethyl, propyl or butyl, and when it is alkanoyl is, for example, formyl, acetyl or propionyl, of which formyl is preferred. Another preferred value for alkanoyl is acetyl. An example of a particularly preferred value for $R^1$ is hydrogen.

A particular value for $R^2$ when it is alkyl is, for example, methyl, ethyl, isopropyl, propyl, butyl or sec-butyl. Another particular value is n-pentyl.

A particular value for Ra when it is alkyl is, for example, methyl or ethyl.

Particular values for optional substituents which may be present when $R^2$ or $R^5$ is phenyl (or on a phenyl, furyl or thienyl moiety attached to alkyl) include, for example:

for alkyl: methyl or ethyl;
for alkoxy: methoxy or ethoxy; and
for halogeno: fluoro, chloro or bromo.

A particular value for a halogenobenzyloxy substituent which may be present on $R^2$ when it is phenyl is, for example, 4-fluorobenzyloxy or 4-chlorobenzyloxy.

A particular value for $R^2$ when it is alkenyl is allyl.

A particular value for $R^2$ when it is phenylalkenyl is 3-phenyl-2-trans-propenyl.

Particular values for $R^2$ when it is 5- or 6-membered heteroaryl include, for example, pyridyl, isoxazolyl or thiadiazolyl.

A particular value for $R^3$ or $R^4$ when it is alkyl is, for example, methyl or ethyl.

A particular value for $R^4$ when it is (alkoxycarbonyl)methyl is, for example, (methoxycarbonyl)methyl or (ethoxycarbonyl)methyl, and when it is (N-alkylcarbamoyl)methyl is, for example, (N-methyl- or N-ethylcarbamoyl)methyl.

A particular value for $R^2$ when it is cycloalkyl is, for example, cyclopropyl, cyclobutyl, cyclopentyl, cyclohexyl or norbornyl, and when it is cycloalkylalkyl is, for example, one of the latter cycloalkyl moieties attached to methyl, ethyl (at position 1 or 2 thereof) or propyl (at position 1, 2 or 3 thereof).

A particular value for $R^2$ when it is phenylalkyl, furylalkyl or thienylalkyl is, for example, benzyl, 1-phenylethyl, 2-phenylethyl, 2-furylmethyl, 3-furylmethyl, 2-thienylmethyl, 3-thienylmethyl or 2-(2-thienyl)ethyl.

Particular values for optional substituents on alkyl when $R^2$ is optionally substituted alkyl (such as methyl or ethyl) include, for example:

for cycloalkyl: cyclopropyl;

for optionally substituted 5- or 6-membered heteroaryl: furyl, pyridyl or thienyl;

for a group of formula $R^{10}(CO)_n Xb(CO)_m$:

for $R^{10}$: methyl, ethyl, n-propyl, cyclohexyl, phenyl or 4-hydroxybenzyl, for Xb: oxy, thio, sulphinyl, imino, methylimino or, together with $R^{10}$, piperidino.

Particular values for optional substituents on phenyl when $R^2$ is optionally substituted phenyl or optionally substituted phenylalkyl (such as 2-phenylethyl) include, for example:

for alkylenedioxy: methylenedioxy;

for halogeno: fluoro, chloro or bromo;

cyano;

trifluoromethyl;

for alkoxycarbonyl: methoxycarbonyl;

hydroxyl for alkanoyloxy: pivaloyloxy;

benzyloxy;

for halogenobenzyloxy: 4-fluorobenzyloxy or 4-chlorobenzyloxy;

nitro;

for alkyl or alkoxy optionally substituted by a group of formula $R^{11}CO$: methyl, methoxy, ethyl ethoxy, 2-(t-butoxycarbonyl)ethyl, methoxycarbonylmethyl, methoxycarbonylmethoxy, 2-(methoxycarbonyl)ethyl, n-propylaminocarbonylmethyl, n-propylaminocarbonylmethoxy, cyclopentylaminocarbonylethyl, cyclohexylaminocarbonylmethyl, [N-methyl, N,N-dimethylaminoethyl]aminocarbonylmethyl or [N-methyl, N,N-dimethylamino]ethyl]aminocarbonylmethoxy; and for sulphamoyl: $-SO_2NH_2$ or $-SO_2N(CH_3)_2$.

A particular value for $R^5$ when it is alkyl is, for example, methyl, ethyl, isopropyl, propyl or butyl.

Particular values for X include, for example, oxy, thio, imino, methylimino or, together with $R^2$, morpholino, thiomorpholino, pyrrolidino, piperidino or azetidino.

A particular value for Xa when it is N-alkylimino is, for example, methylimino, ethylimino or propylimino.

A particularly preferred group of compounds of general formula I consists of those compounds wherein:

Q is 2-furyl;

$R^1$ is hydrogen or acetyl;

$R^2$ is cyclopentyl, cyclohexyl, tetrafluorophenyl, pentafluorophenyl, pyridyl, thiadiazolyl, (4–6C)alkyl, optionally substituted phenyl(1–2C)alkyl, optionally substituted phenyl furylmethyl or pyridylmethyl, any of said optionally substituted phenyl being unsubstituted or substituted by methylenedioxy, or by one of fluoro, chloro, cyano, trifluoromethyl, methoxycarbonyl, hydroxy, pivaloyloxy, nitro, methyl, methoxy, t-butoxycarbonylethyl and sulphamoyl;

X is oxy or imino; A is N or CT in which T is hydrogen; and pharmaceutically acceptable salts thereof.

Of this particularly preferred group of compounds, those wherein $R^2$ is cyclohexyl, tetrafluorophenyl, 2-methylpropyl, phenyl, 2-fluorophenyl, 3-fluorophenyl, 2-chlorophenyl, 3-chlorophenyl, 2-cyanophenyl, 3-cyanophenyl, 2-nitrophenyl, 2-methoxycarbonylphenyl, 2-methoxyphenyl, 3-methoxyphenyl, 2-methylphenyl, 3-methylphenyl, 3-trifluoromethylphenyl, benzyl, 2-fluorobenzyl, 3-methoxybenzyl, 2-furylmethyl, 2-phenylethyl, 2-(4-chlorophenyl)ethyl, 2-(2-methylphenyl)ethyl, 2-(4-t-butoxycarbonylphenyl)ethyl, 2-(4-hydroxyphenyl)ethyl, 2-(4-sulphamoylphenyl)ethyl and 2-(4-pivaloyloxyphenyl)ethyl are especially preferred.

The compounds may be prepared by several different processes. One of these processes comprises reacting a compound of formula II in which Za is a suitable leaving group, for example aryloxy (such as phenoxy) with a compound of formula $R^1NH_2$.

The process is conveniently effected at a temperature in the range of, for example, from 0 to 100° C. Suitable solvents for the process include alcohols such as ethanol and ethers such as tetrahydrofuran. When $R^1$ is hydrogen, it is particularly convenient to employ a solution of ammonia in an alcohol, such as ethanol, or an ether such as tetrahydrofuran at ambient temperature.

The process affords a compound of formula I in which $R^2X$ is an aryloxy group. Since the aryloxy group is capable of functioning as a leaving group, such compounds may be converted into other compounds of formula I by reaction with a compound of the formula $R^2XH$.

This process is generally carried out under basic conditions. These may be conveniently provided by the inherent basicity of the compound of formula $R^2.XH$ itself, for example when X is imino or when $R^2$ contains an amino group Alternatively, the basic conditions may be provided by adding a suitable base to the reaction mixture. Suitable bases include, for example, tertiary amines such as trimethylamine, triethylamine, pyridine, 2,6-dimethylpyridine and 1,8-diazabicyclo[5.4.0]undec-7-ene. It will be appreciated that the basic conditions may also be provided by using the compound of the formula $R^2.XH$ in the form of a salt such as an alkali metal salt, for example, a lithium, sodium or potassium salt. Such a salt may be prepared separately, or formed in situ immediately prior to the above process, by any conventional method, for example by reacting the compound of the formula $R^2.XH$ with an alkali metal (1–4C)alkoxide, hydroxide or hydride in a suitable solvent or diluent such as acetonitrile, 1,2,-dimethoxyethane, -butyl methyl ether, tetrahydrofuran, ethanol or N,N-dimethylformamide.

The process will generally be performed at a temperature in the range, for example, 10 to 120° C. and conveniently in the range 30 to 80° C. and in a suitable solvent or diluent such as acetonitrile, ethanol, tetrahydrofuran, 1,2-dimethoxyethane, t-butyl methyl ether, dimethylsulphoxide or N,N-dimethylformamide.

According to European patent application publication no. 459702A1, the starting materials of formula II may be obtained by dehydrating a compound of formula III. Suitable dehydration agents include, for example, phosphorus pentoxide or a sulphonyl chloride such as p-toluenesulphonyl chloride The dehydration is conveniently effected at a temperature in the range of from 60°–180° C. When phosphorus pentoxide is used, convenient reaction media include the aromatic hydrocarbons such as xylene or toluene. When a sulphonyl chloride is used, convenient solvents include tertiary amines such as pyridine.

The compounds of formula III may be obtained by reacting a compound of formula IV with a compound of formula QCOHal in which Hal is a halogen atom such as a chlorine atom. The reaction is conveniently effected at a temperature in the range of from −10 to 40° C. Suitable solvents for the reaction include halogenated hydrocarbons such as dichloromethane.

The compounds of formula IV may be obtained by reacting a compound of formula V in which Zb is a leaving group, for example halogen atom (such as chlorine) or aryloxy (such as phenoxy) with hydrazine. Alternatively, the compounds of formula III may be obtained by reacting a compound of formula V with a compound of formula QCONHNH$_2$.

Surprisingly, it has now been found that compounds of general formula II (and hence compounds of general formula I) may be prepared from compounds of formula III in substantially improved yield by using a polyphosphoric acid silyl ester as the dehydrating agent.

According to one aspect therefore, the present invention provides a process for the preparation of a 5,7-diaryloxy-2-(2-hetero-aryl)-triazolo[1,5-a][1,3,5]triazine, which comprises reacting a N-2-(4,6-diaryloxy)-[1,3,5]triazinyl-N'-(2-heteroarylcarbonyl)hydrazine with a polyphosphoric acid silyl ester.

The process according to the invention has been found to afford a 5,7-diaryloxy-2-(2-heteroaryl)-triazolo[1,5-a][1,3,5]triazine in substantially higher yield than when either phosphorus pentoxide or a sulphonyl chloride in pyridine is used. Furthermore, the process is more convenient to operate on a large scale than one which employs phosphorus pentoxide because phosphorus pentoxide exists as a sticky mass under the conditions of the reaction.

The reaction is preferably performed in the presence of an inert organic solvent. The solvent may comprise, for example an aromatic hydrocarbon (such as benzene, toluene or a xylene), a halogenated aromatic hydrocarbon (such as chlorobenzene) or sulfolane. Xylenes are particularly preferred solvents for the reaction.

The temperature at which the reaction is performed is conveniently in the range of from 40 to 200° C., preferably from 90 to 150° C.

The number of moles of polyphosphoric acid silyl ester (based on P$_4$O$_{10}$) used per mole of -2-(4,6-diaryloxy)-[1,3,5---triazinyl-N'-(2-heteroarylcarbonyl)hydrazine is preferably in the range of from 0.5 to 10, more preferably from 1 to 5.

The aryl groups in the N-2-(4,6-diaryloxy)-[1,3,5]-triazinyl-N'-(2-heteroarylcarbonyl)hydrazine may be, for example, phenyl groups which are unsubstituted or substituted by 1, 2, or 3 of halogeno (such as fluoro or chloro), (1–4C)alkyl (such as methyl or ethyl), (1–4C)alkoxy (such as methoxy or ethoxy), (1–4C)haloalkyl (such as trifluoromethyl), (1–4C)haloalkoxy (such as trifluoromethoxy), nitro, (1–4C)alkanoyl (such as ethanoyl), (1–4C)alkanoylamino (such as acetamido) and cyano. Most preferably, the aryloxy groups are both phenoxy groups.

The heteroaryl group in the N-2-(4,6-diaryloxy)-[1,3,5]-triazinyl-N'-(2-heteroarylcarbonyl)hydrazine is preferably a furyl group, most preferably a 2-furyl group.

Polyphosphoric acid silyl esters are known reagents, and are sometimes referred to by the initials PPSE. One such reagent, the use of which is particularly preferred in the process according to the invention, is polyphosphoric acid trimethylsilyl ester. This reagent is described in Bull. Chem. Soc, Jpn, 59, 2171–2177 (1986). It may be prepared by reacting phosphorus pentoxide with hexamethyldisiloxane. The reaction is conveniently performed in the presence of an organic solvent, for example a halogenated hydrocarbon (such as methylene chloride) or an aromatic hydrocarbon (for example a xylene). The temperature is conveniently in the range of from 0 to 120° C., e.g. from 0 to 50° C. The number of molar equivalents of hexamethyldisiloxane used per mole of phosphorus pentoxide (measured as P$_4$O$_{10}$) is preferably in the range of from 1 to 10, mole preferably from 1.5 to 4. The solvent, if volatile (such as methylene chloride) may conveniently be removed by evaporation prior to use of the polyphosphoric acid trimethylsilyl ester.

Another polyphosphoric acid silyl ester is a heterogenous reagent that is prepared by reacting phosphorus pentoxide with dry silica gel, as described in Chemistry Letters, 1225–1228, 1982, published by The Chemical Society of Japan.

According to another aspect, the invention provides a process for the preparation of a compound of general formula I as defined hereinabove, which comprises:

(a) reacting a N-2-(4,6-diaryloxy)-[1,3,5]-triazinyl-N'-(2-heteroarylcarbonyl)hydrazine with a polyphosphoric acid silyl ester to afford a compound of formula II in which R2X and Za are aryloxy groups; and (b) reacting the compound of formula II with a compound of formula R$^1$NH$_2$ to afford a compound of formula I in which R$^2$ is an aryloxy group;

followed, if desired by reacting the compound of formula I with a compound of formula R$^2$XH, in which R$^2$ and X have any of the meanings defined hereinabove; and/or forming a pharmaceutically acceptable salt.

The ability of the compounds of formula I to act as an adenosine antagonist may be demonstrated in the following standard A$_2$ Adenosine receptor affinity test:

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (J. Neurochemistry, 1987, 48(2), 498–502).

The membrane preparation is obtained as follows: Frozen pellets of PC12 cells are washed twice with ice cold, buffered, physiological saline and the cells recovered by centrifugation (1500 G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000 G) and the pellet is resuspended in 50 mM tris-HCl buffer, pH 7.4 containing adenosine deaminase (5 units/ml, Type VII from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 µl comprising the test solution or buffer (50 µl), tritiated NECA (50 µl) and membrane suspension (50 µl). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding ($pIC_{50}$).

In general, compounds of the formula I showing antagonist activity in this assay typically show a $pIC_{50}$ in the above test (a) of 6 or more. Thus for example, the compound of Example 2 herein shows a $pIC_{50}$ of about 8. Using the same test procedure, the known compound 1,3-dimethylxanthine typically shows a $pIC_{50}$ of about 5.

The compounds of formula I are generally best administered to warm-blooded animals for therapeutic or prophylactic purposes in the treatment or prevention of cardiovascular diseases and adverse conditions in the form of a pharmaceutical composition comprising said compound of formula I or a pharmaceutically acceptable salt thereof, in admixture or together with a pharmaceutically acceptable diluent or carrier.

In general, it is envisaged that a compound of formula I will be administered orally, intravenously or by some other medically acceptable route (such as by inhalation, insufflation, sub-lingual or transdermal means) so that a dose in the general range, for example, 0.001 mg to 10 (and more particularly in the range, for example, 0.05 to 5 mg/kg) mg/kg body weight is received. However, it will be understood that the precise dose administered will necessarily vary according to the nature and severity of the disease or condition being treated and on the age and sex of the patient.

A composition be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5–200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The following Examples illustrate the invention.

EXAMPLE 1

A mixture of phosphorus pentoxide (1,704 g, 6.0 mmol, as $P_4O_{10}$) and hexamethylenedisiloxane (4.08 ml, 19.2 mmol) was heated under reflux in methylene chloride (3.6 ml) for one hour. Xylene (6.0 ml) was then added, and then the methylene chloride was removed by distillation (final temperature 134° C.). The mixture was then cooled to 100° C., and then N-2-(4,6-diphenoxy)-[1,3,5]triazinyl-N'-(2furoyl)hydrazine (778 mg, 2.0 mmol) was added. The mixture was then heated under reflux for 1.25 hours. The yield of 5,7-diphenoxy-2--(2-furyl)-triazolo[1,5-a][1,3,5]triazine, determined by HPLC, was 73%.

The requisite N-2-(4,6-diphenoxy)-[1,3,5]triazinyl-N'-(2furoyl)hydrazine was prepared as follows A solution of 2,4,6-triphenoxy-1,3,5-triazine (7.2 g) and 2-furoic acid hydrazide (2.5 g) in xylene (60 ml) was heated under reflux for 3 hours. The solvent was then removed by evaporation and the residue was purified by chromatography on silica gel (400 g), eluting with methylene chloride/methanol (2–3%, v/v). A solid was obtained, and this was crystallised from isopropanol to give N-2-(4,6-diphenoxy)-[1,3,5]triazinyl-N'-(2-furoyl)-hydrazine as colourless prisms; m.p. 182°–4° C.; microanalysis; found C, 61.4; H, 3.8; N, 17.7%; $C_{20}H_{15}N_5O_4$ requires C, 61.7; H, 3.9; N, 18.0%; NMR 6.63 (d of d, 1H, 4-furyl H), 7.05–7.5 (complex, 1H, 3-furyl H and phenyl H), 7.87 (s, 1H, 5-furyl H), 9.96 (s, 1H, NH) and 10.34 (s, 1H, NH); m/e 390 $(M+H)^+$.

COMPARATIVE EXAMPLE 1

Preparation of 5,7-diphenoxy-2-(R-furyl)-triazolo[1,5-a[1,3,5]triazine using phosphorus pentoxide N-2-(4,6-Diphenoxy)-[1,3,5]triazinyl-N'-(2-furoyl)hydrazine (2.0 g, 5.1 mmol) was dissolved in xylene (25 ml) at 130° C., and was then cooled to 30° C. Phosphorus pentoxide (5.0 g, 17.6 mmol as $P_4O_{10}$) was then added, and the mixture was then heated under reflux for 7 hours. The mixture was then cooled and left overnight. Ethyl acetate (25 ml) and water (25 ml) were then added, and the organic phase was separated off. The aqueous phase was then extracted with ethyl acetate (25 ml), and the combined organic phases were washed with water and dried with sodium sulphate. The solvent was then evaporated to afford 5,7-diphenoxy-2-(2-furyl)-triazolo[1,5-a][1,3,5]triazine (31%) as an oil which solidified on standing.

EXAMPLE 2

Preparation of 7-amino-2-(2-furyl)-5-phnoxy-[1,2,4]triazolo[1,5-a][1,3,5]triazine A mixture of phosphorus pentoxide (1.136 g, 4.0 mmol, as $P_4O_{10}$) and hexamethylenedisiloxane (1,701 ml, 8.0 mmol) was heated under reflux in methylene chloride (3.6 ml) for one hour. Xylene (6.0 ml) was then added, and then the methylene chloride was removed by distillation (final temperature 134° C.). The mixture was then cooled to 100° C., and then N-2-(4,6-diphenoxy)-[1,3,5]triazinyl-N'-(2-furoyl)hydrazine (1.167 g, 3.0 mmol) was added. The mixture was then heated under reflux for 1.25 hours. It was then diluted with methylene chloride (26 ml) (for HPLC analysis). The solvent was then removed by evaporation, and then methylene chloride (5 ml) and xylene (5 ml) were added. Concentrated aqueous (0.880) ammonia (3.75 ml) was then added slowly, keeping the temperature below 40° C. The mixture was then heated under reflux for 0.5 hour, then cooled, filtered and sucked dry. The resultant solid was crystallised from industrial methylated spirits (20 ml) to afford 7-amino-2-(2-furyl)-5-phenoxy[1,2,4]-triazolo[1,5-a][1,3,5]triazine in 20.6% yield. HPLC analysis of the mother liquors for residual triazolotriazine indicated the total yield for the process was 27.6%.

COMPARATIVE EXAMPLE 2

Preparation of 5,7-diphenoxy. 2?(2-furyl)-triazolo[1,5-a][1,3,5]triazine using p-toluenesulphonyl chloride in pyridine N-2-(4,6-Diphenoxy)-[1,3,5]triazinyl-N'-(2-furoyl)hydrazine (1.0 g, 2.57 mmol) was heated at 100° C. with p-toluenesulphonyl chloride (0.74 g, 3.88 mmol) in pyridine (30 ml) overnight. A further portion of p-toluenesulphonyl chloride (0.74 g, 3.88 mmol) was then added. The resultant mixture was left at 100° C. for one hour, and was then heated under reflux for 1.5 hours, by which time all of the starting material had disappeared. The solvent was then removed by evaporation, and the resultant oil was dissolved in methylene chloride (50 ml) and washed with water (3×30 ml). The methylene chloride was then removed by evaporation, then the residue was dissolved in a 50% v/v mixture of methylene chloride and toluene, and then this solvent was removed by evaporation. The residual oil was then dissolved in industrial methylated spirits (50 ml), and the resultant solution was saturated with gaseous ammonia. The mixture was then allowed to stand over the weekend, and was then saturated again with gaseous ammonia, and then heated under reflux for one hour. The solvent was then removed by evaporation to afford a solid. HPLC analysis of the product indicated a yield of only 14.6%.

EXAMPLE 3

Conversion of 7-amino-2-(2-furyl)-5-phenoxy-[1,2,4]triazolo[1,5-a][1,3,5]triazine into another compound of formula I A solution of 7-amino-2-(2-furyl)-5-phenoxy-[1,2,4]triazolo[1,5-a][1,3,5]triazine (1.01 g) and tyramine (1.43 g) in dimethylformamide (40 ml) was stirred at 100° C. until tlc analysis indicated that most of the phenoxy starting material had disappeared (2-3 hours). The solvent was removed in vacuo and the residue purified by chromatography on silica (100 g) eluting with ethyl acetate. The solid (1.3 g) obtained was crystallised from ethyl acetate to give 7-amino-2-(2-furyl)-5-[2-(4-hydroxyphenylethyl]-amino[1,2,4]triazolo[1,5-a][1,3,5]triazine as colourless prisms m.p. 222°-225° C.; microanalysis, found: C,56.6; H,5.1; N,26.4%; $C_{16}H_{15}N_7O_2.0.33$ $C_4H_8O_2$ requires: C,56.8; H,4.8; N,26.7%; NMR: 2.75(t,2H, $CH_2$ Ar), 3.4(t,2H, $CH_2N$), 6.7 (complex 3H, furyl-4H+phenyl-H), 7.05 (complex, $^3H$, furyl-3H +phenyl-H), 7.4-7.6(dt,1H, NH), 7.85(d, 1H, furyl-5H), 8.0-8.5(broad d,2H, $NH_2$), 9.15(s,1H, OH), the spectrum also contained signals due to ethyl acetate (0.33 mole); m/e 338 $(M+H)^+$.

EXAMPLE 4

Preparation of 7-amino-2-(2-furyl)-5-phenoxy-[1,2,4]triazolo[1,5-a][1,3,5]triazine Hexamethyldisiloxane (3.0 mole) is charged to a slurry of phosphorus pentoxide (1.5 mole, measured as $P_4O_{10}$) in xylene. The mixture is then heated to 90° C. over 1.5 hours and then stirred for 1 hour at 90° C. during which time all of the solid dissolves. N-2-(4,6-diphenoxy)-[1,3,5]triazinyl]-N'-(2-furoyl)hydrazine (1.0 mole) is then charged to the solution and the temperature is increased to reflux. The solid dissolves, but during the course of the cyclisation a second solid is precipitated. The cyclisation is normally complete in 2.5 hours at which point the mixture is cooled to 25° C., and can for convenience be held overnight. Acetonitrile is then added and the temperature reduced to 15° C. Water is then added. The mixture is then cooled back to 15° C. and 0.91 ammonia solution is added, keeping the temperature below 25° C. Once the addition is complete the temperature is increased to 40° C. for 1 hour. The reaction mixture is then cooled to 25° C., the solid filtered off and washed with a large volume of water. The yield is approximately 85%.

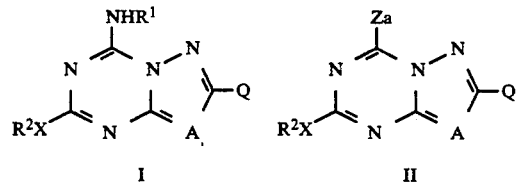

-continued $$\underset{\text{III}}{\underset{R^2X}{\overset{Z_a}{\diagdown}}\underset{N}{\overset{N}{\diagdown}}\underset{NHNHCOQ}{\overset{N}{\diagdown}}} \qquad \underset{\text{IV}}{\underset{R^2X}{\overset{Z_a}{\diagdown}}\underset{N}{\overset{N}{\diagdown}}\underset{NH_2NH_2}{\overset{N}{\diagdown}}}$$

$$\underset{V}{\underset{R^2X}{\overset{Z_a}{\diagdown}}\underset{N}{\overset{N}{\diagdown}}\underset{Z_b}{\overset{N}{\diagdown}}}$$

What is claimed is:

1. A process for the preparation of a compound of formula II, $$\underset{R^2X}{\overset{Z_a}{\diagdown}}\underset{N}{\overset{N}{\diagdown}}\underset{A}{\overset{N-N}{\diagdown}}Q \qquad \text{II}$$

which comprises reacting a compound of formula III $$\underset{R^2X}{\overset{Z_a}{\diagdown}}\underset{N}{\overset{N}{\diagdown}}\underset{NHNHCOQ}{\overset{N}{\diagdown}} \qquad \text{III}$$

with a polyphosphoric acid silyl ester; wherein

Q is selected from the group consisting of furyl, thienyl, oxazolyl, thiazolyl, isoxazolyl and isothiazolyl, optionally bearing 1 or 2 substituents independently selected from (1–4C)alkyl and halogeno;

$R^2X$ is aryloxy; and $Z_a$ is aryloxy.

2. A process as claimed in claim 1, in which the reaction is performed at a temperature in the range of from 40 to 200° C.

3. A process as claimed in claim 1 or claim 2, in which the reaction is performed in the presence of a solvent selected from aromatic hydrocarbons, halogenated aromatic hydrocarbons and sulfolane.

4. A process as claimed in claim 3, in which the solvent is a xylene.

5. A process as claimed in claim 1 or claim 2, in which the polyphosphoric acid silyl ester is polyphosphoric acid trimethylsilyl ester.

6. A process as claimed in claim 5, in which the polyphosphoric acid trimethylsilyl ester has been prepared by reacting phosphorus pentoxide with hexamethyldisiloxane in an amount of from 1 to 10 molar equivalents of hexamethyldisiloxane per mole of phosphorus pentoxide (measured as $P_4O_{10}$).

7. A process as claimed in claim 1 or claim 2, in which the number of moles of polyphosphoric acid silyl ester (based on $P_4O_{10}$) used per mole of the compound of formula III is in the range of from 0.5 to 10.

8. A process as claimed in claim 1 or claim 2, wherein the aryloxy groups $R^2X$ and $Z_a$ are phenoxy groups which are unsubstituted or substituted by 1, 2, or 3 or halogeno, (1–4C)alkyl, (1–4C)alkoxy, (1–4C)haloalkyl, (1–4C)haloalkoxy, nitro, (1–4C)alkanoyl, (1–4C)alkanoylamino and cyano; and Q is a 2-furyl group.

9. A process as claimed in claim 8, in which the aryloxy groups are both phenoxy groups.

10. A process as claimed in claim 1, wherein Q is 2-furyl.

11. A process for the preparation of a compound of formula I or a pharmaceutically acceptable salt thereof $$\underset{R^2X}{\overset{NHR^1}{\diagdown}}\underset{N}{\overset{N}{\diagdown}}\underset{A}{\overset{N-N}{\diagdown}}Q \qquad \text{(I)}$$

wherein

Q is selected from the group consisting of furyl, thienyl, oxazolyl, thiazolyl, isoxazolyl and isothiazolyl, optionally bearing 1 or 2 substituents independently selected from (1–4C)alkyl and halogeno;

$R^1$ is hydrogen, (1–6C)alkyl, or (1–4C)alkanoyl;

$R^2$ is hydrogen, (3–12C)cycloalkyl, (3–6C)alkenyl, phenyl(3–6C)alkenyl, tetrafluorophenyl, pentafluorophenyl, pyridyl, isoxazolyl, thiadiazolyl, optionally substituted (1–6C)alkyl or optionally substituted phenyl, wherein said optionally substituted alkyl is unsubstituted or substituted with one or (3–6C)cycloalkyl, optionally substituted 5- or 6-membered heteroaryl wherein said heteroaryl is selected from furyl, pyridyl and thienyl, optionally substituted phenyl and a group of formula $R^{10}(CO)_nXb(CO)_m$;

wherein $R^{10}$ is (1–6C)alkyl, (3–6C)cycloalkyl, optionally substituted phenyl or optionally substituted phenyl(1–4C)alkyl;

wherein $n+m$ is 0 or 1, provided that when m is 0, X and Xb are separated by at least two carbon atoms;

wherein Xb is oxy, thio, sulphinyl, sulphonyl or an imino group of formula —NRb in which Rb is hydrogen, (1–6C)alkyl or together with $R^{10}$ and the adjacent nitrogen atom forms a 4 to 6-membered saturated heterocyclic ring;

wherein said optionally substituted 5- or 6-membered heteroaryl selected from furyl, pyridyl and thienyl is unsubstituted or substituted with 1 or 2 of (1–4C)alkyl, (1–4C)alkoxy and halogeno; and wherein any of said optionally substituted phenyl is unsubstituted or substituted by (1–4C)alkylenedioxy or by 1, 2 or 3 of halogeno, cyano, trifluoromethyl, (1–4C)alkoxycarbonyl, hydroxy, (1–4C)alkanoyloxy, benzyloxy, halogenobenzyloxy, nitro, and (1–4C)alkyl or alkoxy optionally bearing a group of formula $R^{11}CO$;

wherein $R^{11}$ is (1–4C)alkoxy, (3–6C)alkylamino, (3–6C)cycloalkylamino or [N-(1–4C)alkyl][N-(1–4C)dialkylamino(1–4C)alkyl]amino, and sulphamoyl of formula —$SO_2.NR^3R^4$ wherein $R^3$ and $R^4$ are independently hydrogen or (1–4C)alkyl, or $R^3$ is hydrogen and $R^4$ is [(2–5C)alkoxycarbonyl]methyl, carbamoylmethyl or [N-(1–4C)alkylcarbamoyl]methyl; and wherein X is oxy, thio, sulphinyl, sulphonyl or an imino group of formula —NRa— is which Ra is hydrogen, (1–6C)alkyl or together with $R_2$ and the adjacent nitrogen atom forms a 4 to 6-membered saturated heterocyclic ring; and wherein A is N;

which process comprises the steps of (a) reacting a N-2-(4,6-diaryloxy)-[1,3,5]triazinyl-N'-(heteroarylcarbonyl)hydrazine with a polyphosphoric acid silyl ester to afford a compound of formula II

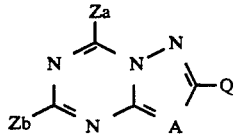 (II)

in which Za and Zb ar aryloxy groups;

(b) reacting the compound of formula II with a compound of formula R¹NH₂ to afford a compound of formula VI,

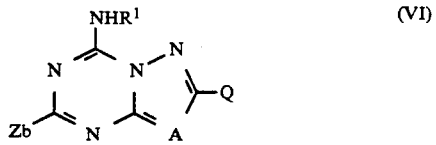 (VI)

where Zb is an aryloxy group; and (c) reacting the compound of formula VI with a compound of formula R²XH to form a compound of formula I.

* * * * *